(12) United States Patent
O'Lenick et al.

(10) Patent No.: US 8,158,114 B1
(45) Date of Patent: *Apr. 17, 2012

(54) ALKOXYLATED CITRATE POLYESTERS HAVING LIQUID AND SOLID DOMAINS

(75) Inventors: Kevin A. O'Lenick, Dacula, GA (US); Andrew J. O'Lenick, Dacula, GA (US); Anthony J. O'Lenick, Jr., Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 375 days.

This patent is subject to a terminal disclaimer.

(21) Appl. No.: 12/586,709

(22) Filed: Sep. 28, 2009

(51) Int. Cl.
*A61K 8/72* (2006.01)
*A61K 8/02* (2006.01)

(52) U.S. Cl. .................................. 424/70.11; 424/401

(58) Field of Classification Search ................ None
See application file for complete search history.

(56) References Cited

U.S. PATENT DOCUMENTS

| 4,868,236 A | * | 9/1989 | O'Lenick, Jr. | 524/308 |
| 5,089,658 A | * | 2/1992 | Elmore et al. | 560/182 |
| 7,049,476 B1 | * | 5/2006 | O'Lenick, Jr. | 568/852 |

* cited by examiner

*Primary Examiner* — Brian Gulledge

(57) ABSTRACT

The present invention is directed to a series of water soluble polymeric citrate esters that have two different molecular weight ester chains, one solid and one liquid, which when combined into a single molecule make a polymer that is solid, but has very unique flow properties. These materials find applications as additives to aqueous, hydroalcoholic or emulsion formulations in personal care products where there is a desire to have a structured film (provided by the solid fatty group) and flow properties, (provided by the liquid fatty group).

15 Claims, No Drawings

US 8,158,114 B1

ALKOXYLATED CITRATE POLYESTERS HAVING LIQUID AND SOLID DOMAINS

RELATED APPLICATIONS

This application claims priority to and benefit of U.S. Provisional Application No. 61/279,259 filed Jul. 20, 2009, the disclosure of which is incorporated herein for all purposes.

FIELD OF THE INVENTION

The present invention is directed to a series of alkoxylated polymeric citrate esters that have two different molecular weight ester chains, one solid and one liquid, which when combined into a single molecule make a polymer that is solid, but has very unique surfactant properties. These materials find applications in aqueous, hydroalcoholic, and emulsion systems as additives to formulations in personal care products where there is a desire to have a structured film (provided by the solid fatty group) and flow properties, (provided by the liquid fatty group). These compounds by virtue of their unique structure provide outstanding skin feel upon drying. These combinations of properties make the compounds of great interest in sun care, skin care and pigmented products.

BACKGROUND OF THE INVENTION

Citric acid is a common material of natural origin. The structure is:

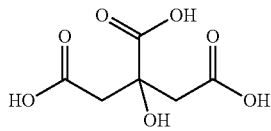

CAS Registry Number: 77-92-9
CA Index Name: 1,2,3-Propanetricarboxylic acid, 2-hydroxy- Citric acid is made by fermentation, using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in Physiology or Medicine for the discovery. The series of reactions is known by various names, including the citric acid cycle, the Krebs cycle, and the tricarboxylic acid cycle Citrate esters are known. They conform to the following structure:

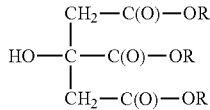

The esters are made by the reaction of fatty alcohols with citric acid.

U.S. Pat. No. 4,292,192 issued to Hooper, et al. teaches that Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

U.S. Pat. No. 2,122,716 describes long chain esters of citric acid, e.g., tridodecyl citrate, which have been used as plasticizers for resinous compositions.

U.S. Pat. Nos. 3,239,555 and 3,241,992 disclose bis-citric acid esters made by esterifying the acid groups with C1 to C18 alcohols and coupling the esters with dibasic acids. Such esters are useful as plasticizers for plastics.

U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

U.S. Pat. No. 5,089,658 issued Feb. 18, 1992 to Elmore et al, is directed to citric acid esters. In one aspect, this invention pertains to citric acid esters which contain at least one primary or secondary hydroxyl group. In another aspect, this invention relates to citric acid esters which are reactive diluents. In still another aspect, this invention pertains to citric esters which are pigment dispersants.

The citric ester compositions of this invention are useful as reactive diluents for high solids thermosetting coating composition and as pigment dispersants for use in thermosetting coatings.

U.S. Pat. No. 4,868,236 to O'Lenick discloses a guerbet citric ester and polymers thereof useful in plastic lubrication.

None of these patents provide water loving polyester derivatives of mixed fatty esters of citrate as envisioned by the present invention.

THE INVENTION

Objective of the Invention

The present invention has as its objective a series of citrate polyesters that have both liquid and solid fatty groups contained thereon and are crosslinked by water soluble diols and contain fatty groups, one solid at room temperature, the other liquid at room temperature.

The present invention also has as an objective a process for treating hair and skin with the citrate multi domain polyesters that have both liquid and solid fatty groups contained thereon and are crosslinked by the water soluble diol.

Other objectives will become clear as one reads the specification and claims herein.

SUMMARY OF THE INVENTION

The present invention discloses a polyester made by the reaction of a mixture of liquid and solid fatty acids reacted with citric acid and a water soluble diol crosslinker.

DETAILED DESCRIPTION OF THE INVENTION

The present invention relates to a polyester that conforms to the following structure:

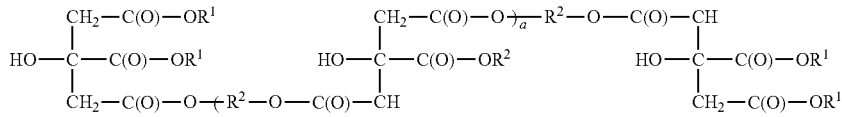

$R^1$ is a mixture of between 15 and 60%

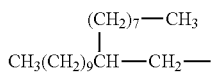

and between 40 and 85% —$(CH_2)_d$—$CH_3$
b is an integer ranging from 11 to 31 (resulting in solid domains);
$R^2$ is —$(CH_2CH_2O)_x$—$CH_2CH_2$—;
x is an integer ranging from 8 to 75;
a is an integer ranging from 0 to 20.

Another aspect of the present invention is a process for conditioning hair and skin which comprises contacting the hair or skin with an effective conditioning concentration of a polyester that conforms to the following structure:

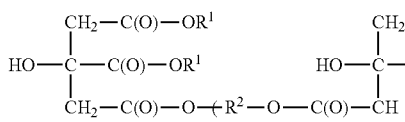 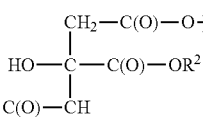

$R^1$ is a mixture of between 15 and 60%

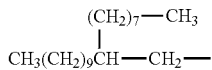

and between 40 and 85% —$(CH_2)_d$—$CH_3$
d is an integer ranging from 11 to 31 (resulting in solid domains);
$R^2$ is —$(CH_2CH_2O)_x$—$CH_2CH_2$—;
x is an integer ranging from 8 to 75;
a is an integer ranging from 0 to 20.

In a preferred embodiment said effective conditioning concentration ranges from 0.1% to 20% by weight.

The products of the present invention are made by the esterification reaction of:
(a) citric acid conforming to the following structure:

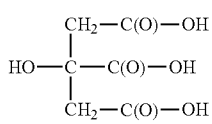

(b) a water soluble diol conforming to the following structure;

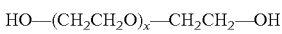

X is an integer ranging from 8 to 75;
(c) octyldodecanol conforming to the following structure:

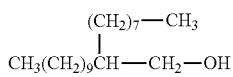

resulting in liquid high molecular weight domains
(d) a fatty alcohol that is solid at room temperature

d is an integer ranging from 11 to 31 (resulting in solid domains).

Another aspect of the present invention is a process for conditioning hair and skin which comprises contacting the hair or skin with an effective conditioning concentration of a polyester made by the esterification reaction of:

(a) citric acid conforming to the following structure:

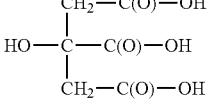

(b) a water soluble diol conforming to the following structure;

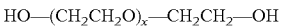

x is an integer ranging from 8 to 75;
(c) octyldodecanol conforming to the following structure:

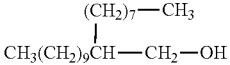

resulting in liquid high molecular weight domains

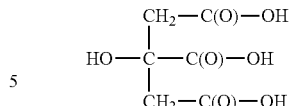

(d) a fatty alcohol that is solid at room temperature

d is an integer ranging from 11 to 31 (resulting in solid domains).

Where there are two different types of ester group present, one liquid and one solid, the resulting structure cannot crystallize completely, since the liquid domains in the polymer act as molecular crystal distorters, resulting in a polymer that although having the same melting point, flows more easily when pressure is applied. The resulting solid will be soft and flowable, rather than hard and un-yielding. The presence of the water soluble diol increases the water solubility and allows for the delivery of this outstanding skin feel from aqueous emulsions, hydroalcoholic solutions or emulsions (regular or invert), providing upon dry down an excellent feel heretofore unattainable in non oil systems.

PREFERRED EMBODIMENTS

In a preferred embodiment a is an integer ranging from 1 to 20.
In a preferred embodiment a is an integer ranging from 3 to 10.
In a preferred embodiment a is 10.
In a preferred embodiment a is 15.

EXAMPLES

Example 1

Citric Acid

Citrate is an item of commerce commercially available from a variety of sources including Pfizer. It conforms to the following structure:

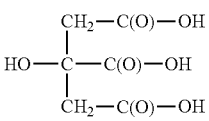

Examples 2-5

Water Soluble Diols

The water soluble diols useful in the present invention are items of commerce sold by many suppliers and conforming to the following structure:

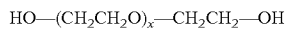
HO—(CH₂CH₂O)ₓ—CH₂CH₂—OH x is an integer ranging from 8 to 75.

| Example | x |
|---------|----|
| 2 | 8 |
| 3 | 10 |
| 4 | 50 |
| 5 | 75 |

In the present invention this material provides a linking group that is (a) water soluble, (b) based upon polyoxyethylene, polyoxypropylene compounds, and mixtures thereof, and (c) are easily reacted into the polymer matrix.

In the present invention this material provides a linking group that is (a) natural, (b) free of polyoxyethylene and polyoxypropylene compounds and their inherent ether groups and lack of natural origin, and (c) are easily reacted into the polymer matrix.

Example 6

Octyldodecanol

Octyldodecanol is a Guerbet alcohol commercially available from a variety of sources including Cognis.

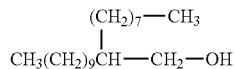

Examples 7-12

Fatty Alcohols (Solid at Room Temperature)

These acids are an item of commerce available from a variety of sources. It conforms to the following structure;

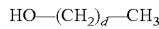
HO—(CH₂)_d—CH₃ d is an integer ranging from 11 to 31.

| Example | d |
|---------|----|
| 7 | 11 |
| 8 | 13 |
| 9 | 15 |
| 10 | 17 |
| 11 | 19 |
| 12 | 31 |

To a suitable reactor equipped with heating and an ability to distill off water is added the specified number of grams of citrate acid (Example 1), next is added the specified number of grams of the octyldodecanol (Examples 6). Finally, is added the specified number of grams of the specified solid fatty alcohol (Examples 7-12). The reaction mass is heated to 150-160° C. and water is distilled off. As the reaction proceeds, the batch clears and free citric acid is reacted out. The reaction mass is kept at this temperature until the acid value becomes vanishingly low. Next is added the specified number of grams of the specified diol (Examples 2-5). The reaction mass is heated to 180-190° C. and water is distilled off. The reaction mass is kept at this temperature until the acid value becomes vanishingly low. The reaction mass is cooled and used without additional purification.

| | Citric Acid Example 1 | Diol Example 2-5 | | Guerbet Example 6 | Solid Alcohol Example 7-12 | | a |
|---------|-------|-----|-------|-------|-----|-------|-------|
| Example | Grams | Ex. | Grams | Grams | Ex. | Grams | value |
| 10 | 138 | 2 | 140 | 433 | 7 | 402 | 1 |
| 11 | 165 | 3 | 585 | 465 | 8 | 331 | 2 |
| 12 | 150 | 4 | 1827 | 301 | 9 | 486 | 5 |
| 13 | 150 | 5 | 3256 | 353 | 10 | 423 | 10 |
| 14 | 148 | 2 | 385 | 410 | 11 | 365 | 15 |
| 15 | 124 | 3 | 155 | 327 | 12 | 483 | 20 |

Ex means example in the table above.

Products that are of the present invention were low order soft water soluble surface active agents, which upon dry down do not have the traditional sticky feel of standard surfactants. Those products that were made using only solid fatty acids were hard solids that were not spreadable on the skin or hair.

The compounds are of exceptional interest in the personal care applications where gloss, rheology that accommodates spreading and odor are critical.

The compounds of the present invention in addition to their unique aesthetics when used in cosmetic formulations, most importantly sunscreens.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A polyester made by the esterification reaction of:

(a) citric acid conforming to the following structure:

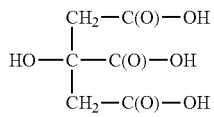

(b) a water soluble diol conforming to the following structure;

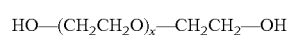

x is an integer ranging from 8 to 75;

(c) octyldodecanol conforming to the following structure:

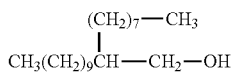

resulting in liquid high molecular weight domains; and
(d) a fatty alcohol that is solid at room temperature

wherein d is an integer ranging from 11 to 31 (resulting in solid domains).

2. A process for conditioning hair and skin which comprises contacting the hair or skin with an effective conditioning concentration of a polyester made by the esterification reaction of:
(a) citric acid conforming to the following structure:

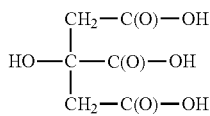

(b) a water soluble diol conforming to the following structure;

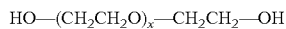

x is an integer ranging from 8 to 75;

(c) octyldodecanol conforming to the following structure:

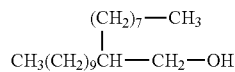

resulting in liquid high molecular weight domains; and
(d) a fatty alcohol that is solid at room temperature

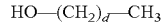

wherein d is an integer ranging from 11 to 31 (resulting in solid domains).

3. A process of claim 1 wherein said effective conditioning concentration ranges from 0.1% to 20% by weight.
4. A polyester of claim 1 wherein d is 11.
5. A polyester of claim 1 wherein d is 13.
6. A polyester of claim 1 wherein d is 15.
7. A polyester of claim 1 wherein d is 16.
8. A polyester of claim 1 wherein d is 19.
9. A polyester of claim 1 wherein d is 31.
10. A process of claim 3 wherein d is 11.
11. A process of claim 3 wherein d is 13.
12. A process of claim 3 wherein d is 15.
13. A process of claim 3 wherein d is 16.
14. A process of claim 3 wherein d is 19.
15. A process of claim 3 wherein d is 31.

* * * * *